United States Patent
Simard et al.

(10) Patent No.: US 9,683,973 B2
(45) Date of Patent: Jun. 20, 2017

(54) METHOD AND SYSTEM OF CONSOLIDATING MULTIPLE PHASED ARRAY INSTRUMENTS

(71) Applicants: Christian Simard, Quebec (CA); Benjamin Couillard, Quebec (CA)

(72) Inventors: Christian Simard, Quebec (CA); Benjamin Couillard, Quebec (CA)

(73) Assignee: Olympus Scientific Solutions Americas Inc., Waltham, MA (US)

(*) Notice: Subject to any disclaimer, the term of this patent is extended or adjusted under 35 U.S.C. 154(b) by 206 days.

(21) Appl. No.: 14/801,399

(22) Filed: Jul. 16, 2015

(65) Prior Publication Data

US 2016/0025686 A1    Jan. 28, 2016

Related U.S. Application Data

(60) Provisional application No. 62/029,051, filed on Jul. 25, 2014.

(51) Int. Cl.
| | |
|---|---|
| *G01N 29/07* | (2006.01) |
| *G01N 29/36* | (2006.01) |
| *G01N 29/26* | (2006.01) |
| *G01N 29/34* | (2006.01) |
| *G01N 29/28* | (2006.01) |

(52) U.S. Cl.
CPC ........... *G01N 29/36* (2013.01); *G01N 29/262* (2013.01); *G01N 29/341* (2013.01); *G01N 29/348* (2013.01); G01N 29/07 (2013.01); G01N 29/28 (2013.01); G01N 2291/02854 (2013.01); G01N 2291/044 (2013.01); G01N 2291/106 (2013.01)

(58) Field of Classification Search
CPC ................................. G01N 2291/044
USPC .......................................... 73/628
See application file for complete search history.

(56) References Cited

U.S. PATENT DOCUMENTS

| | | | | |
|---|---|---|---|---|
| 5,494,038 A | * | 2/1996 | Wang | A61B 8/0866 |
| | | | | 600/459 |
| 6,536,553 B1 | * | 3/2003 | Scanlon | G01N 29/069 |
| | | | | 181/108 |

(Continued)

FOREIGN PATENT DOCUMENTS

WO    2010/017445 A3    4/2010

OTHER PUBLICATIONS

A. McNab., M.J. Campbell, (Abstract) Ultrasonic phased arrays for nondestructive testing, SAO/NASA, Dec. 1987, 2 pages.*

(Continued)

*Primary Examiner* — Clayton E Laballe
*Assistant Examiner* — Kevin Butler
(74) *Attorney, Agent, or Firm* — C. Tricia Liu (57) ABSTRACT

A non-destructive testing and inspection (NDT/NDI) system and method operable to conduct an ultrasonic scanning test on a test object that synchronizes and merges the apertures of two or more NDT sub-instruments in frequency and phase. Disclosed are a method of using a Phased Lock Loop (PLL) as a synchronizing clock/trigger generator, and also a method of using a General Positioning Clock (GPS) and a pulse per second (PPS) output. Both methods combine ultrasonic scanning data acquisition from two or more NDT sub-instruments, and transform the sub-instruments into one bigger NDT instrument.

24 Claims, 9 Drawing Sheets

(56) References Cited

U.S. PATENT DOCUMENTS

| | | | | |
|---|---|---|---|---|
| 6,813,950 B2* | 11/2004 | Glascock | ............ | G01N 29/221 73/622 |
| 9,279,785 B2* | 3/2016 | Zhang | ................... | G01N 29/07 |
| 2004/0016299 A1* | 1/2004 | Glascock | ............ | G01N 29/221 73/638 |
| 2011/0126626 A1* | 6/2011 | Koch | ................... | G01N 29/07 73/632 |
| 2014/0352436 A1* | 12/2014 | Zhang | ................... | G01N 29/07 73/598 |
| 2017/0030869 A1* | 2/2017 | Ungerer | ................ | G01N 29/04 |

OTHER PUBLICATIONS

Holmes, Caroline et al., Advanced post-processing for scanned ultrasonic arrays: Application to defect detection and classification in non-destructive evaluation, Ultrasonics 48, Aug. 20, 2008, 7 pages.*

Holmes, Caroline, Post-processing of the full matrix of ultrasonic transmit—receive array data for non-destructive evaluation, NDT&E International 38, Jan. 24, 2005, 11 pages.*

D.M. McCann et al., Review of NDT methods in the assessment of concrete and masonry structures, NDT&E International 34, 2001, 14 pages.*

Bruce W. Drinkwater et al., Ultrasonic arrays for non-destructive evaluation: A review, NDT&E 39, May 22, 2006, 17 pages.*

ISA, A Method and System of Consolidating Multiple Phased Array Instruments PCT US2009/053096, Written Opinion of ISA, Mar. 2, 2010, 3 pages.*

ISA, A Method and System of Consolidating Multiple Phased Array Instruments PCT US2009/053096, Search Report, Aug. 7, 2009, 3 pages.*

A technical paper published on the Cornell University web site ("Multi-Channel Data Acquisition with Absolute Time Synchronization" by P. Wlodarczyk, S. Pustelny, D. Budker, and M Lipiński) at http://arxiv.org/ftp/arxiv/papers/1311/1311.5849.pdf , published in the US.

* cited by examiner

METHOD AND SYSTEM OF CONSOLIDATING MULTIPLE PHASED ARRAY INSTRUMENTS

CROSS-REFERENCE TO RELATED APPLICATIONS

This application claims the benefit and priority of U.S. Provisional patent application Ser. No. 62/029,051 filed Jul. 25, 2014 entitled A METHOD AND SYSTEM OF CONSOLIDATING MULTIPLE PHASED ARRAY INSTRUMENTS, the entire disclosure of which is incorporated herein by reference.

FIELD OF THE INVENTION

This invention relates to non-destructive testing and inspection (NDT/NDI) technology instruments, and more particularly to a system and method of consolidating a group of phased array NDT instruments, each with different measuring apertures, any one or more of which may be selected by the user.

BACKGROUND OF THE INVENTION

A typical problem in phased array ultrasound (PAUT) NDT inspection utilizing multiple instruments is combining the data from multiple inspection instruments and obtaining phase-synchronous and frequency-synchronous data. Typically, the inspection instruments are neither synchronized in frequency nor in phase, making it hard to match the data from one instrument with another since they are not on the same time-base.

As the acquisition time gets longer, the problem is exacerbated. Assuming that one sub-instrument is the true time, the other sub-instruments acquire data slightly faster or slower. Thus, even if the data is synchronized using one particular NDT inspection feature, another inspection feature acquired at a later time is likely to be unsynchronized.

Inspection events with NDT instruments are often time critical. Having to adjust the phase and frequency of inspection features from multiple instruments can distract the effort of an inspection operator. Patent WO2010/017445A3 disclosed an apparatus that aims to increase the aperture of a medical ultrasound system using add-on ultrasound systems. However, clock synchronization is not performed. Instead, synchronization is performed by comparing the timing of received pulses from the different add-on instruments. This method is not good enough for industrial purposes because in industrial NDT data acquisition the acquisition time can be much longer, and time slip is more likely to occur. If one particular feature is time synchronized among multiple instruments, a feature acquired at a later time is likely to be unsynchronized because of the time slip.

A technical paper published on the Cornell University web site ("Multi-Channel Data Acquisition with Absolute Time Synchronization" by P. Wlodarczyk, S. Pustelny, D. Budker, and M. Lipiński) at http://arxiv.org/ftp/arxiv/papers/1311/1311.5849.pdf discloses a method to synchronize multiple channels of data on remote acquisition cards with absolute time synchronization. However, the application described in the paper is different from the one described in the present disclosure, and the sampling rate is about a thousand times slower. In contrast, the present invention deals with the most acute problems of consolidating data from multiple unsynchronized instruments.

Considering the background information above, a solution that provides a plurality of NDT instruments to service providers, while minimizing or eliminating manual adjustment of multiple phases and frequencies, would be of great utility and economic value.

SUMMARY OF THE INVENTION

It is a general object of the present disclosure to overcome the problems associated with the background art by introducing a system and method of consolidating the apertures of multiple NDT instruments by synchronizing or compensating the sub-instruments both in frequency and in phase, wherein the aperture merging between the sub-instruments is seamless at the instrument supervisor level. Several embodiments are herein proposed to achieve this goal.

It is further an object of the present disclosure to overcome the problems associated with the background art by introducing a method and system that contains NDT instruments with different probes and apertures, any one of which may be selected by the user as the basis for the sole phase and frequency.

It is further an object of the present disclosure to maintain the integrity of the factory or service center calibration when switching between the aperture of one NDT sub-instrument to another.

It is further an object of the present disclosure to minimize the number of phase and frequency adjustments by combining them in such a way as to be shared by at least two or more NDT sub-instruments.

It is yet a further object of the present disclosure to provide a convenient manual or semi-automatic means of phase and frequency adjustment to allow the other NDT sub-instruments to configure themselves to work properly with the selected NDT sub-instrument's phase and frequency.

These and other objects of the present disclosure can be realized with a PAUT NDT instrument comprising multiple sub-instruments, wherein the NDT instrument includes: hardware and software compatible with the NDT sensor technology; a means to preserve calibration integrity when one NDT sub-instrument's phase and frequency is switched to follow another; a user interface suitable for each NDT sub-instrument's aperture; a sensor connection means allowing sharing among different NDT instrument apertures; and a means to automatically detect the aperture type and to configure the instrument to operate in a suitable manner.

Other features and advantages of the present invention will become apparent from the following description of the invention which refers to the accompanying drawings.

BRIEF DESCRIPTION OF THE OF THE DRAWINGS

FIG. 8b shows the cross-correlation result after correction of the out-of-phase data in FIG. 8a.

DETAILED DESCRIPTION OF THE INVENTION

This invention is an apparatus for combining together and synchronizing or compensating the apertures of multiple PAUT NDT instruments so that the multiple instruments behave as one combined instrument. The invention is capable of other embodiments and may be practiced in various ways. Thus, it should be understood that the invention is not limited in its application to the details of construction and the arrangements of components set forth in the following description, or illustrated in the drawings. The embodiments described herein and the claims described hereof are not to be read restrictively unless there is clear and convincing evidence manifesting a certain exclusion, restriction, or disclaimer.

Figure 1:
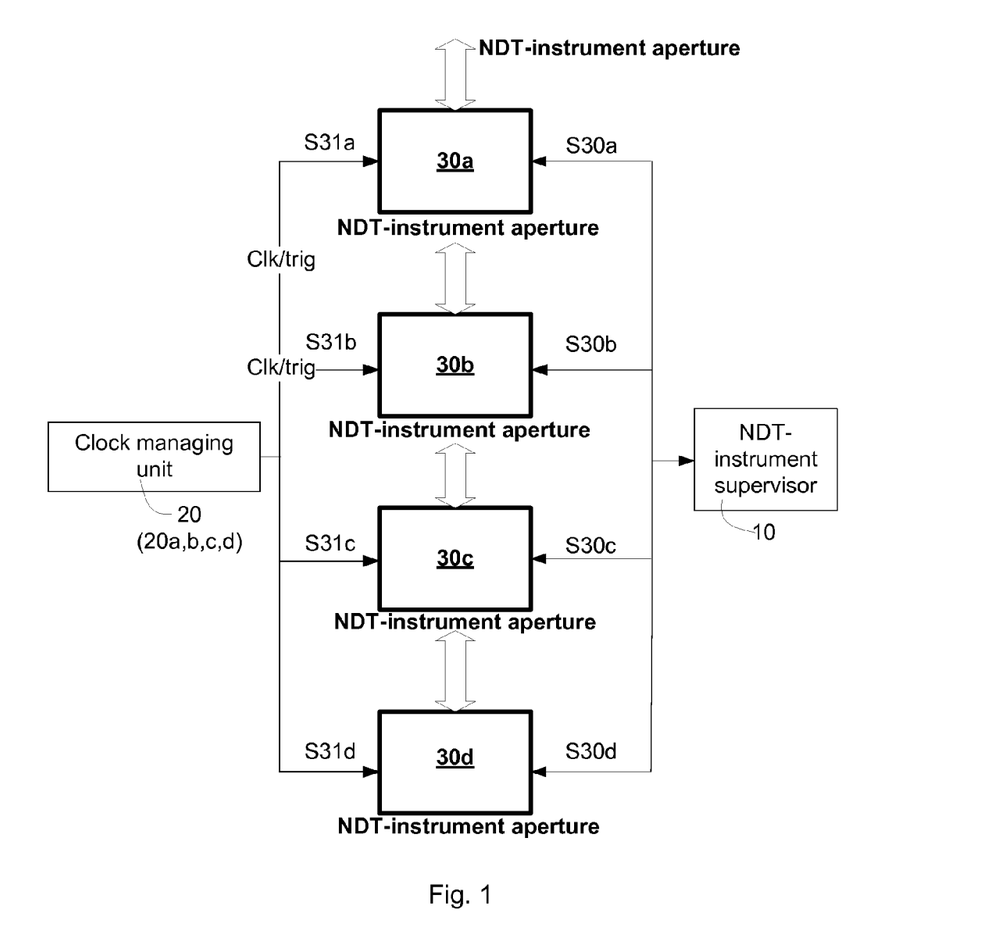
FIG. 1 is a schematic view of the consolidated PAUT system with a supervisor instrument and its sub-instrument components according to the present disclosure.

Referring to FIG. 1, the consolidated PAUT system of the present disclosure comprises preferably an NDT-instrument supervisor 10, sub-instruments 30a, 30b, 30c, and 30d, a clock managing unit 20 for each of the sub-instruments (20a for sub-instrument 30a, 20b for sub-instrument 30b, 20c for sub-instrument 30c, 20d for sub-instrument 30d, each of them sending respective clock/trigger signals S31a, S31b, S31c, and S31d). Sub-instruments 30a, 30b, 30c, and 30d are connected by data links S30a, S30b, S30c, and S30d. The specific components of this system are described in greater detail in FIGS. 4 and 7. Four (4) sub-instruments are shown along with NDT-instrument supervisor 10, but this design can be applied to more than 4 sub-instruments.

Clock managing unit 20 has clock/trigger signals S31a, S31b, S31c, and S31d, which must be shared by all 4 sub-instruments 30a, 30b, 30c, and 30d. Clock managing unit 20 distributes both a clock and a trigger signal. The clock signal is distributed to all the sub-instruments to ensure that each sub-instrument acquires the ultrasound data at the same rate, thus making the 4 sub-instruments synchronous in frequency, but not necessarily in phase. The purpose of the trigger signal is to synchronize the start of the data acquisition for all the sub-instruments.

In the exemplary solution, clock managing unit 20 is an external stand-alone device, but the synchronizing clock and trigger generator can be internal to one of the sub-instruments and distributed to other sub-instruments, or it could be distributed from NDT-instrument supervisor 10. The variations of this configuration are all within the scope and teaching of the present disclosure. Another key part is the configuration of data links S30a, S30b, S30c, and S30d between NDT-instrument supervisor 10 and sub-instruments 30a, 30b, 30c, and 30d, respectively. The function of the NDT-instrument supervisor is further explained in FIG. 2.

Continuing with FIG. 1, NDT-instrument supervisor 10 has two (2) main functions. The first function of NDT-instrument supervisor 10 is to configure the aperture of each sub-instrument (30a, 30b, 30c, or 30d) according to the sub-instrument type, the type of material to be inspected, the geometry of the part to be inspected, and also according to the relative placement of the sub-instruments' probes. The second function of the NDT-instrument supervisor 10 is to combine the data sent by all the sub-instruments, effectively merging their respective apertures into one aperture bigger than that of one sub-instrument in a seamless way.

Figure 2:
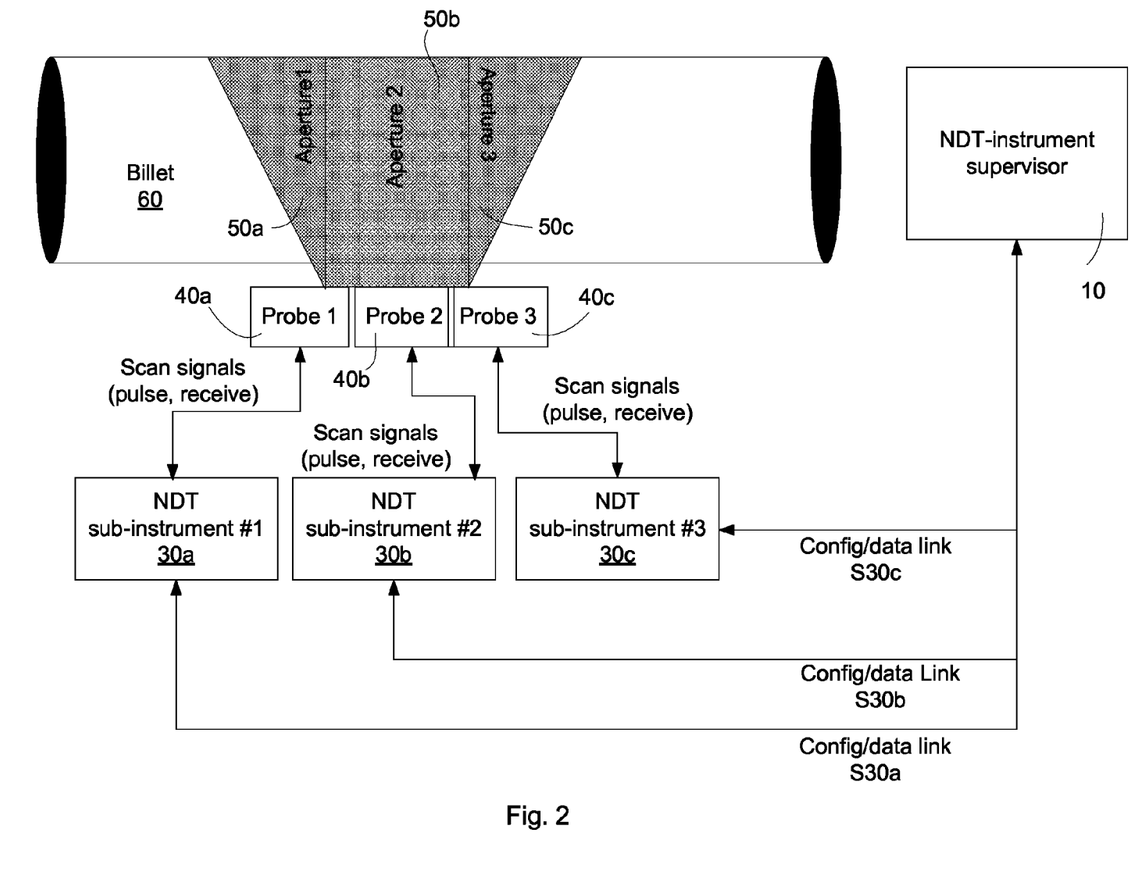
FIG. 2 is a schematic view of the PAUT instrument of the present disclosure, including the supervisor instrument and its sub-instrument software/firmware modules, showing how they relate to an NDT inspection.

Referring now to FIG. 2, an example of an NDT inspection setup using three (3) sub-instruments 30a, 30b, and 30c, and NDT-instrument supervisor 10 is shown. As in FIG. 1, configuration and data links S30a, S30b, and S30c between NDT-instrument supervisor 10 and sub-instruments 30a, 30b, and 30c are shown. Clock managing unit 20 is omitted for clarity. One of the key components of the invention is the placement of NDT probes 40a, 40b, and 40c connected to their respective sub-instruments 30a, 30b, and 30c, along with the scan areas of their respective apertures 50a, 50b, and 50c, on an inspected steel billet 60. The area covered by one sub-instrument's aperture does not overlap with the area covered by another sub-instrument's aperture. Therefore, when the apertures are merged by NDT-instrument supervisor 10, the combined aperture covers a much greater area than that of one sub-instrument.

First, NDT-instrument supervisor 10 configures each sub-instrument (30a, 30b, and 30c) according to the sub-instrument's type, the type of material to be inspected, the geometry of the part to be inspected, and the relative placement of the sub-instruments' probes. Configuring a sub-instrument includes, but is not limited to, configuring the sub-instrument's pulser voltage, pulse width, pulser delays, the receiver's acquisition duration, acquisition delays, analog filters, and digital filters.

Second, NDT-instrument supervisor 10 combines the data sent by all sub-instruments (30a, 30b, and 30c), effectively merging their respective apertures into one bigger aperture. This bigger aperture allows the user to inspect more volume and area of the inspected part in less time. Effectively, all the sub-instruments work as a combined NDT instrument.

Figure 3:
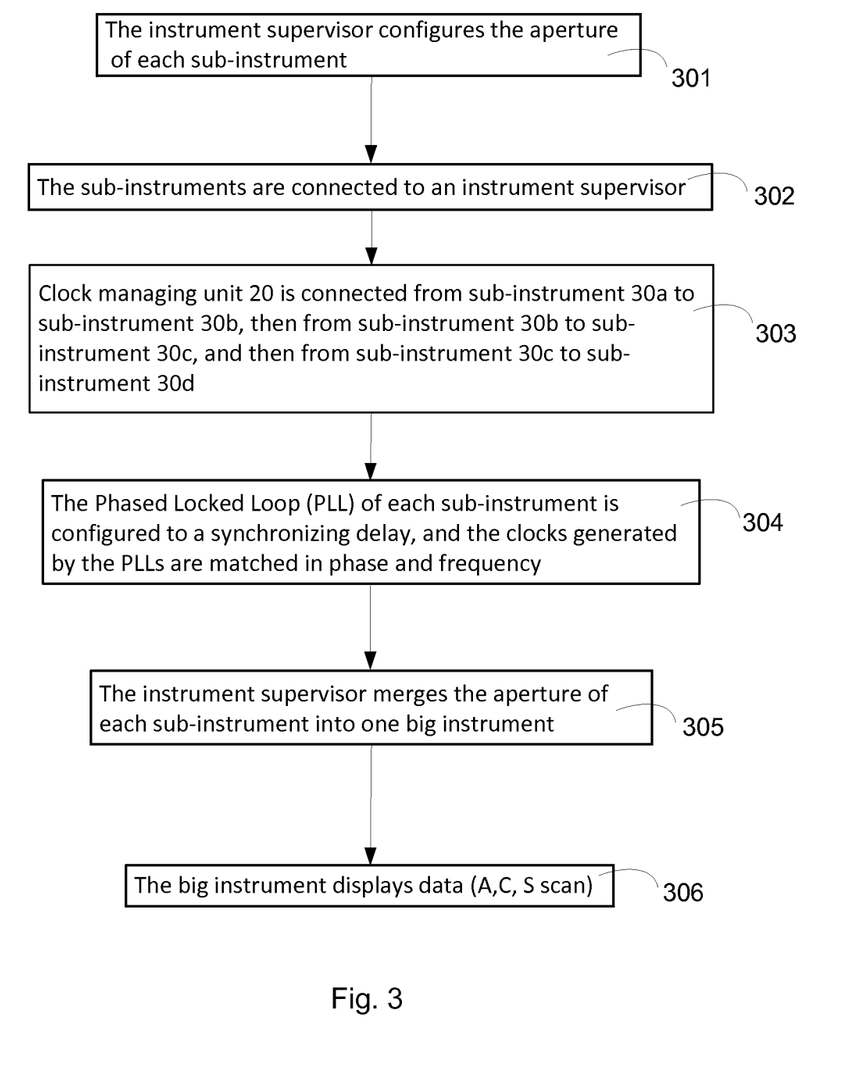
FIG. 3 is a flow chart view illustrating set-up and test of the instrument, supervisor and sub-instruments, using a clock generator and a Phase-Locked Loop (PLL).

Reference is now made to FIG. 3, which is a flow chart view of the process of setting up the NDT sub-instruments, and performing an NDT test according to the present disclosure, using clock managing unit 20 which can be designed in a number of ways. One of the novel aspects of the present invention is to use a Phase-Locked Loop (PLL) to generate both sampling clocks and synchronizing clocks. Therefore the PLL functions as a clock/generator module shown later in FIG. 4 as 210a and 210b.

The PLL is a widely used electronic component and a novelty of the present disclosure includes configuring the PLL for the purpose of synchronizing phase for the present invention.

In step 301, NDT-instrument supervisor 10 configures each sub-instrument and each of their apertures. In step 302, the sub-instruments are connected to NDT-instrument supervisor 10. In step 303, clock managing unit 20 is connected from sub-instrument 30a to sub-instrument 30b, from sub-instrument 30b to sub-instrument 30c, and from sub-instrument 30c to sub-instrument 30d. The PLL of each sub-instrument is configured to a synchronizing delay in step 304, and the clocks of the PLLs of each sub-instrument are matched in phase and frequency, which is described in greater detail in FIG. 6. In step 305, once the sub-instruments are matched in phase and frequency, NDT-instrument supervisor 10 merges the respective apertures of the sub-instruments into one consolidated PAUT system shown in FIG. 1. This consolidated system then displays scan data in step 306 via NDT-instrument supervisor 10.

Figure 4:
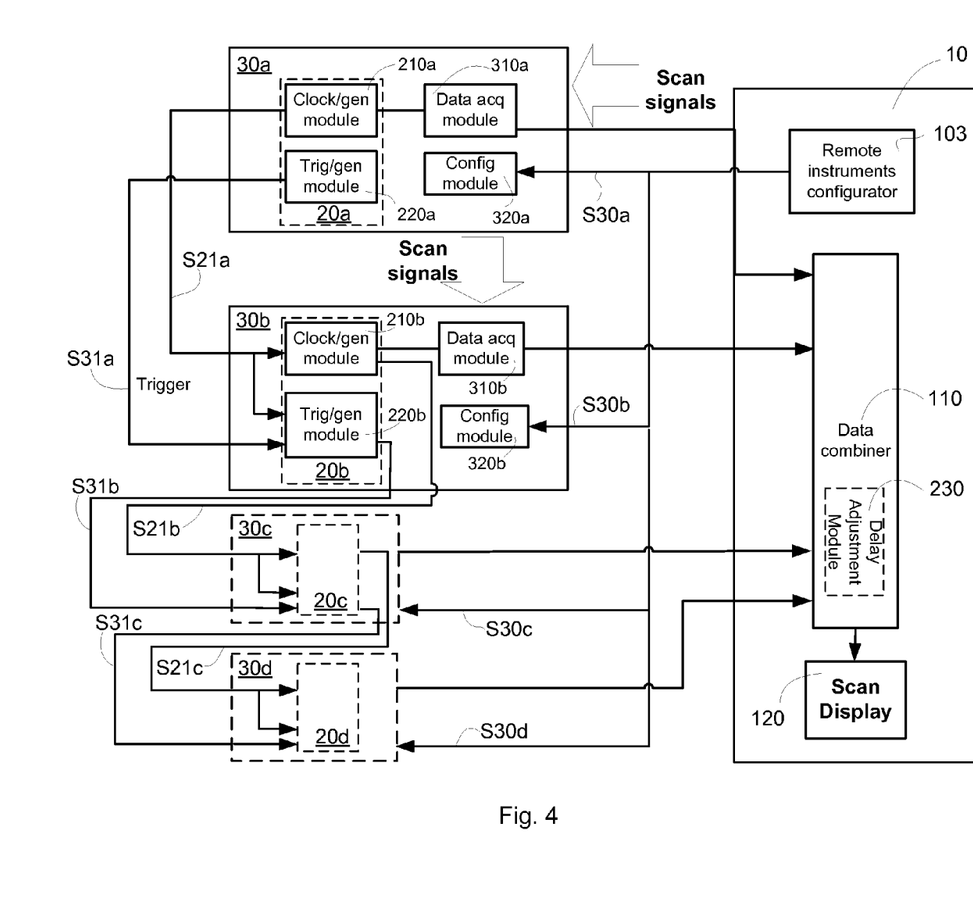
FIG. 4 is a schematic view of the supervisor instrument and sub-instrument interconnections of the present disclosure, using a clock generator and a PLL.

Referring to FIG. 4, one of the novel aspects of the present disclosure is the interconnections between NDT-instrument supervisor 10 and the sub-instruments, using a clock generator and/or the PLL as described in association with FIG. 3. In FIG. 4 the consolidated PAUT system is shown in a more detailed view than in FIG. 1. As can be seen, sub-instrument 30a is further comprised of a clock/generator module 210a and a trigger/generator module 220a, a data acquisition module 310a, and a configuration module 320a. Similarly sub-instrument 30b is further comprised of a clock/generator module 210b and a trigger/generator module 220b, a data acquisition module 310b, and a configuration module 320b.

It can also be noted in FIG. 4 that clock managing unit 20 in FIG. 1 is further presented as clock/generator module 210a and a trigger/generator module 220a in sub-instrument 30a, and clock/generator module 210b and a trigger/generator module 220b in sub-instrument 30b, respectively. For simplicity and clarity, the clock/generator modules and trigger/generator modules of sub-instruments 30c and 30d are not shown in FIG. 4.

Clock/generator module 210a, trigger/generator module 220a, clock/generator module 210b, and trigger/generator module 220b are daisy chained. Sub-instrument 30a in the daisy-chain firstly generates a synchronizing clock, 20 MHz in this exemplary case, from an oscillator, which is fed to the clock/gen module 210a, which is preferably a PLL as previously described.

Continuing with FIG. 4, NDT-instrument supervisor 10 is further comprised of a remote instruments configurator 103, a data combiner 110, a scan display module 120, and optionally a delay adjustment module 230.

The functions of clock/generator module 210a are preferably fulfilled by a PLL, which uses a 20 MHz clock, as an exemplary case, from the oscillator (external, not shown) to generate all the sampling clock signals S21 for sub-instruments 30a, 30b, 30c, and 30d, as well as a 20 MHz synchronizing clock signal 521a for daisy chained clock/generator module 210b and trigger/generator module 220b that are within sub-instrument 30b, the next remote sub-instrument. Sub-instrument 30a in the chain also generates trigger signal S31a at a rate dictated by NDT-instrument supervisor 10. Delay adjustment module 230 stores calibration data compensating the delay between 20a and 20b, and retrieves the calibration data to adjust the 20 MHz clock of sub-instrument 30a, as described in greater detail in FIG. 5.

Trigger signal S31a from sub-instrument 30a is used to start the data acquisition of sub-instrument 30b. This trigger signal is fed to sub-instrument 30b, the first sub-instrument in the chain. The process is then repeated for sub-instrument 30c, and extended to sub-instrument 30d. The process can be extended to more sub-instruments, and is limited only by the phase matching error buildup, the data rate limitations, and processing power limitations of NDT-instrument supervisor 10. A 20 MHz clock is the exemplary clock for the disclosure, but this process can be used with a different frequency.

Figure 4A:
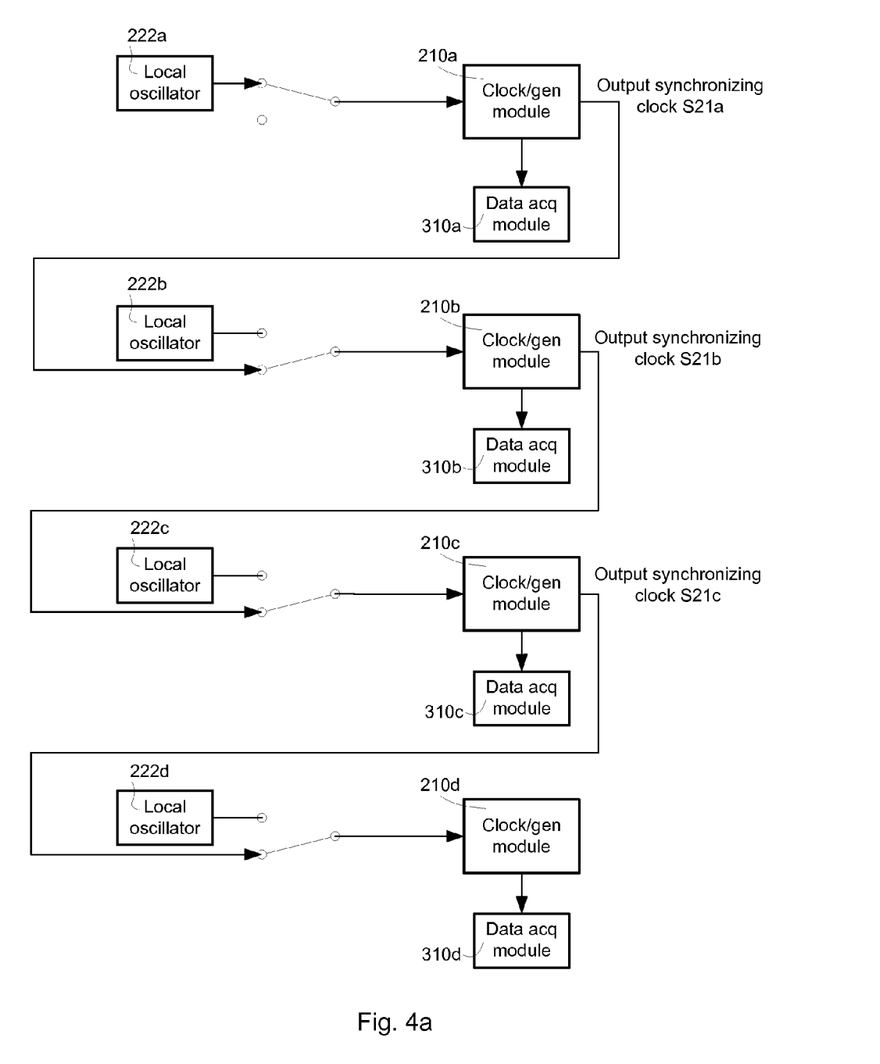
FIG. 4a is a schematic view showing details of the daisy-chain sub-instrument interconnections.

Referring to FIG. 4a, preferably each sub-instrument is configured to have an oscillator on board, namely 222a, 222b, 222c and 222d, respectively. These oscillators serve to provide the basis of the internal clocks of each sub-instrument. The specific operating clock used in a particular inspection operation may be chosen to be either the original internal clock, or the adjusted clock based on a synchronizing clock. It should be noted that one consolidated oscillator can also be shared by the sub-instruments.

The clock from a local oscillator is fed to the PLL only if there is no input from a synchronizing clock. As shown in FIG. 4a, only the first sub-instrument uses the oscillator 222a for its PLL input, while the other sub-instruments use the synchronizing clock signals from the previous sub-instrument.

Figure 5:
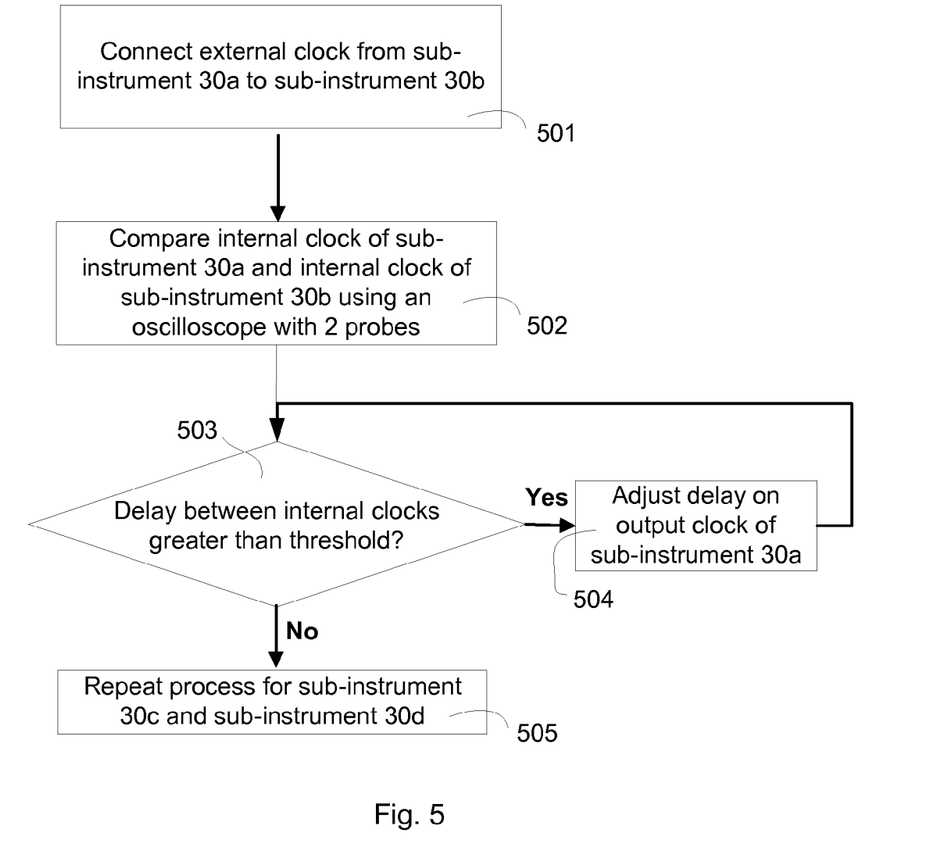
FIG. 5 is a flow chart view of the steps of a factory PLL calibration.

Referring now to FIG. 5, a flow chart view of the steps of a factory PLL configuration/calibration is shown, using a PLL that functions as clock managing unit 20. This flow chart is an example of a factory calibration of NDT sub-instruments done by an operator to determine a PLL configuration such that in the consolidated system all synchronizing clocks of each sub-instrument are in phase. The PLL of each sub-instrument uses clock managing unit 20 to generate synchronizing clocks 20a, 20b, 20c, and 20d. Three types of clocks are involved in the functions of the PLL: synchronizing clocks generating signals 21a, 21b, 21c respectively which are external to sub-instruments 2, 3 and 4; the internal clocks of each sub-instrument which are adjusted by the respective up-stream synchronizing clock and are the clocks in operation when a sub-instrument becomes the operating clock; and lastly the output clocks of sub-instruments 30a, 30b, 30c, and 30d (which are the internal clocks of the sub-instruments, adjusted for cable transmission delays). 20 MHz is the exemplary clock frequency for this disclosure, but this process can be used with a different frequency.

In step 501, the output clock of sub-instrument 30a is connected to sub-instrument 30b. Sub-instrument 30a does not have an input synchronization clock, because it is the first sub-instrument in the chain. For sub-instruments 30b, 30c, and 30d, the clock used as the PLL input is the input synchronization clock, while for sub-instrument 30a the clock used is its internal 20 MHz clock. Since sub-instrument 30b uses the output synchronization clock of sub-instrument 30a, the synchronizing clock of 30b has the same frequency as that of 30a, but is likely out of phase because of cable and transmission delays.

In order to determine the phase of the various signals, it is necessary to sample the signals at a sampling clock frequency which may be any convenient multiple of the synchronization clock frequency. In the present embodiment, a 100 MHz sampling clock frequency is used, but this process can be used with a different frequency.

Continuing with FIG. 5, in step 502 the phase delay between the synchronizing clocks of sub-instruments 30a and 30b is measured, and stored in delay adjustment module 230 in NDT-instrument supervisor 10. In step 503, it is determined if the cumulative delay exceeds a certain threshold (for example 500 picoseconds). If yes, then in step 504 a delay adjustment for the output clock signal is performed. In the context of FIG. 4, if the phase delay is greater than a determined threshold, then delay adjustment module 230 retrieves the stored phase delay data and adjusts the output clock of sub-instrument 30a in step 504 (providing a synchronizing clock signal S21a) until the phase difference is within the threshold.

Still in step 504, the delay on the output synchronization clock is adjusted on sub-instrument 30a, until its internal 20 MHz clock signal and the internal 20 MHz clock signal of sub-instrument 30b have a delay less than the determined tolerance (500 picoseconds in the present example). Once performed, the internal clocks of sub-instrument 30a and sub-instrument 30b are matched both in frequency and in phase.

In step 505 the process is repeated between sub-instrument 30b and sub-instrument 30c, between sub-instrument 30c and sub-instrument 30d, and so on for any number of sub-instruments. Once performed, the internal clocks of all the sub-instruments are matched in both frequency and phase.

Figure 6:
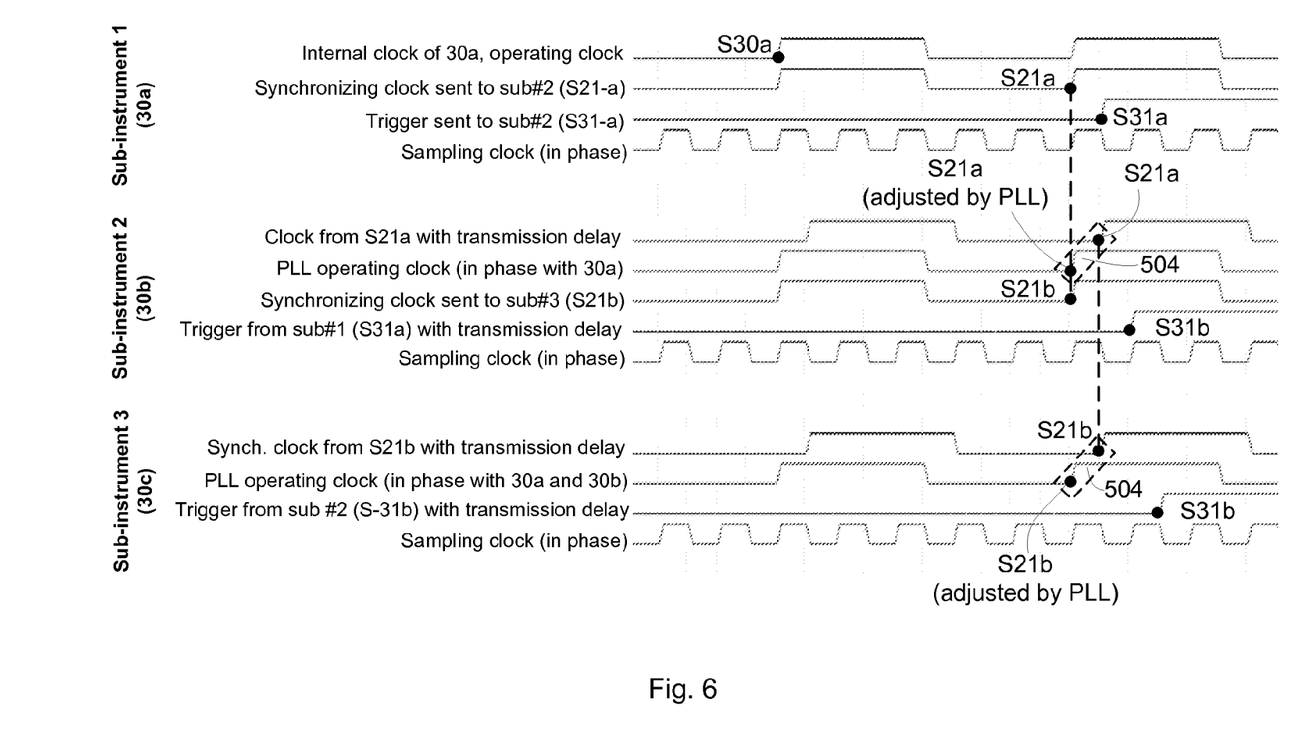
FIG. 6 is a grouped depiction of synchronizing clocks, triggers, and PLLs for each sub-instrument, using a clock generator and a PLL.

Reference is now made to FIG. 6, which explains the phase relationship between synchronizing clock signals S21a and S21b, trigger signals S31a and S31b, and the associated functions of the PLL. FIG. 6 also shows, for each sub-instrument, a sampling clock signal, a trigger signal from another sub-instrument with a time delay, a PLL clock in phase with another sub-instrument, and a synchronizing clock signal with or without a transmission delay for sub-instruments 30a, 30b, and 30c. For simplicity and clarity, the signals for sub-instrument 30d have been omitted.

In FIG. 6, the sampling clocks of all the sub-instruments have the same frequency and the same phase, because the PLL of each sub-instrument is adjusted for the buffer and the cable transmission delays during the calibration process. This is essential for the synchronization. The sampling clock of each sub-instrument is phase-locked to its respective 20 MHz internal clock, but ticking at a higher rate, e.g., 100 MHz.

As shown in FIG. 6, three groups of waveforms are associated with sub-instruments 30a, 30b and 30c respectively. The groups of waveforms in the subsequent description can be referred to as "top group," "middle group," and "bottom group" for description purposes. Waveforms from sub-instrument 30d are omitted for the sake of simplicity. It should also be noted that the sequence of the sub-instruments and their associated waveforms are arbitrarily presented here, and any alternative arrangement is within the scope of the present disclosure.

As seen in the top group of waveforms, sub-instrument 30a has data link S30a from NDT-instrument supervisor 10, and a sampling clock that is in phase with sub-instrument 30b and sub-instrument 30c. It also has trigger signal S31a sent to sub-instrument 30b, and synchronizing clock signal S21a that is also sent to sub-instrument 30b. Since it is the first instrument in the chain, it does not receive an input synchronization clock as do the other sub-instruments. Its internal clock is the operating clock. Synchronizing clock signal S21a from sub-instrument 30a is generated from clock/generator module 210a, and trigger signal S31a is generated by trigger/generator module 220a, and both signals are sent to sub-instrument 30b.

As seen in the middle group of waveforms, sub-instrument 30b has a sampling clock that is in phase with sub-instrument 30a and sub-instrument 30c, as well as a PLL that is configured to be in phase with sub-instrument 30a. Synchronizing clock signal S21a from sub-instrument 30a with a transmission delay is received by sub-instrument 30b. This delay is adjusted by the PLL of clock/generator module 210b (more specifically, by step 504), and presented as waveform "PLL operating clock (in phase with 30a)", which is the operating clock for 30b. Synchronizing clock signal S21b is generated from clock/generator module 210b. Trigger signal S31b is generated by trigger/generator module 220b, which is distributed to sub-instrument 30c. As can be seen, trigger signal S31b and synchronizing clock signal S21b are sent to sub-instrument 30c.

Continuing with FIG. 6, specifically the bottom group of the waveforms, sub-instrument 30c has a sampling clock that is in phase with sub-instrument 30b and sub-instrument 30a, as well as a PLL that is configured to be in phase with sub-instrument 30b and sub-instrument 30a. Synchronizing clock signal S21b from sub-instrument 30b is received with a transmission delay by sub-instrument 30c. This delay is adjusted by the PLL of the clock/generator module of sub-instrument 30c (more specifically, by step 504; the clock/generator module of sub-instrument 30c is not shown in FIG. 4 for simplicity purposes), and presented as waveform "PLL operating clock (in phase with 30a and 30b)", which is the operating clock of 30c. Trigger signal S31b is also sent from sub-instrument 30b with a transmission delay.

Figure 7:
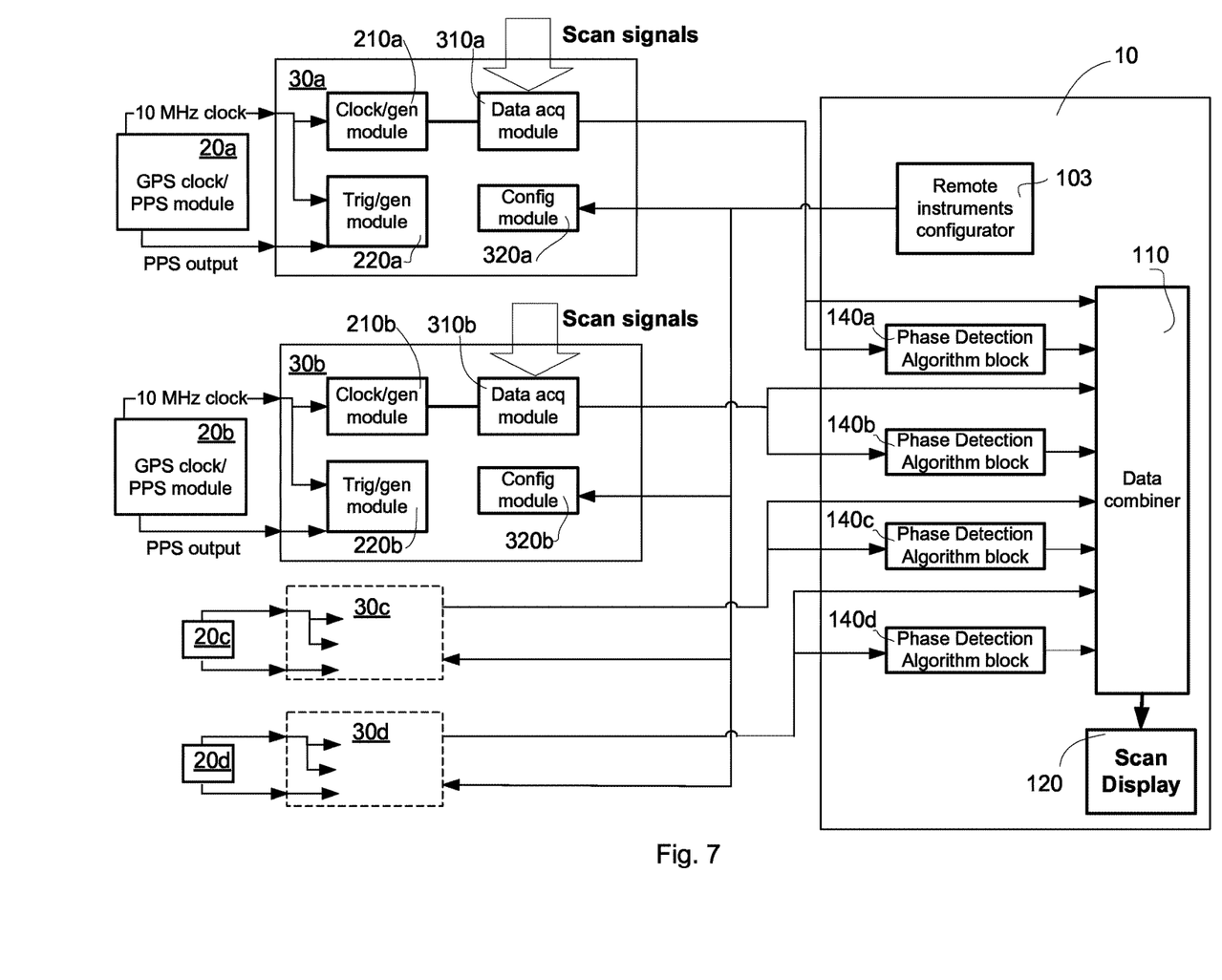
FIG. 7 is a schematic view of the NDT-instrument supervisor instrument and sub-instrument interconnections of the present disclosure, using a clock derived from a wireless connection with the Global Positioning System (GPS) and a pulse per second (PPS) output.

Referring to FIG. 7, another of the novel aspects of the present invention is a method to merge apertures by using a Global Positioning System (GPS) clock and a pulse per second (PPS) output. This method is embodied by having GPS clock/PPS modules 20a, 20b, 20c and 20d act as clock managing units 20 for sub-instruments 30a, 30b, 30c, and 30d. In the exemplary embodiment, GPS clock/PPS module 20a uses the commonly available GPS signal to generate a 10 MHz-clock and 1 pulse every second for trigger/generator module 220a. The 10 MHz clock is used for a maximum acquisition duration of 10 milliseconds in the present embodiment, although different maximum acquisition duration times are also within the scope of the invention. For a maximum acquisition duration of 10 milliseconds, the phase and timing of the clock/generators can be considered to be the same for each remote sub-instrument, since a time slip between 2 sub-instruments can be considered negligible on such a time scale.

However in this embodiment the sub-instruments are not phase-locked, since there is significant jitter between the synchronizing pulses per second of the different GPS modules. To work around this problem, a phase detection process is disclosed, which is comprised of NDT-instrument supervisor 10, data acquisition module 310a of sub-instrument 30a, data acquisition module 310b of sub-instrument 30b, and Phase Detection Algorithm blocks 140a, 140b, 140c, and 140d to synchronize the data acquisition start time of each sub-instrument. In FIG. 7, data acquisition modules for sub-instruments 30c and 30d are not shown for the sake of simplicity.

Continuing with FIG. 7, each sub-instrument starts the data acquisition at the same time delay after receiving its respective pulse per second input, and, in the present embodiment, data acquisition continues for 10 milliseconds. Each sub-instrument's 10 MHz clock can be considered to be locked in frequency; however significant jitter exists between each of the pulse per second inputs, and the sub-instruments are not yet phase-synchronous.

Once the acquisition is completed by the data acquisition modules, the data is sent to NDT-instrument supervisor 10. The NDT-instrument supervisor synchronizes the data by comparing the first indications found on the Phase Detection Algorithm blocks 140a, 140b, 140c, and 140d of each sub-instrument 30a, 30b, 30c, and 30d.

Figure 8A:
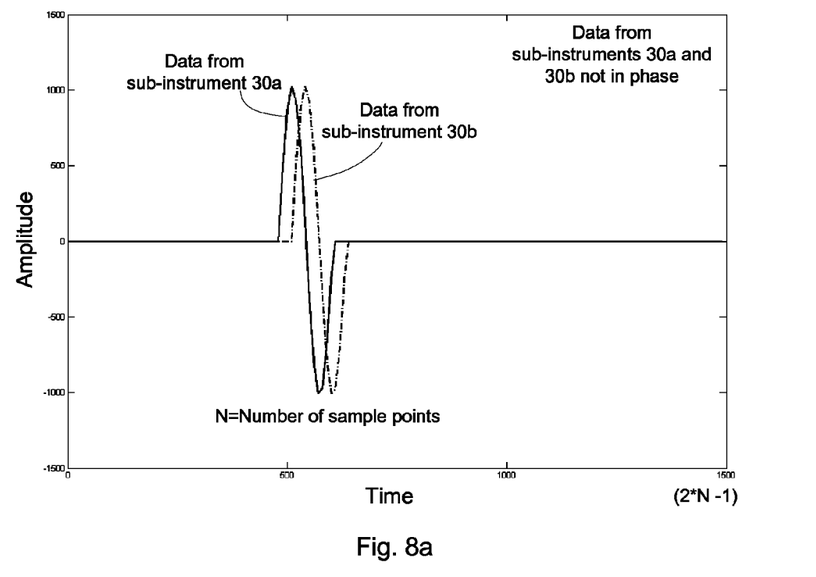
FIG. 8a shows sample points taken from two different sub-instrument components.
Figure 8B:
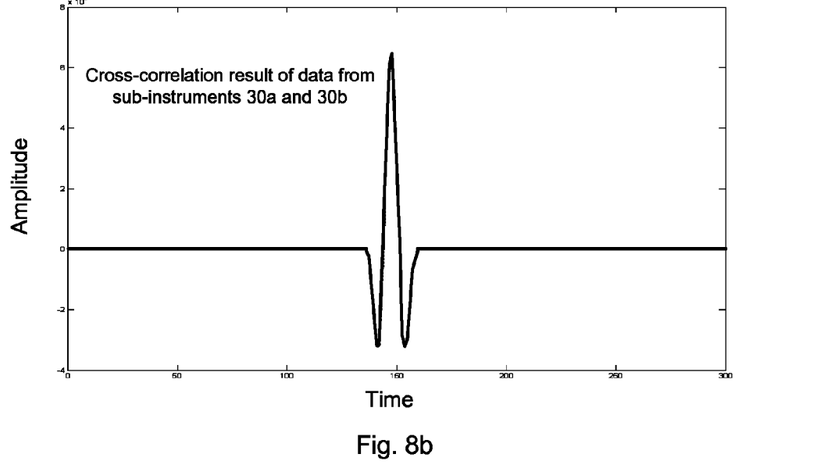

Reference is now made to FIGS. 8a and 8b, which illustrate use of a cross-correlation mathematical function which enables measurement of the relative time delay between the different sub-instruments using algorithms for Phase Detection Algorithm blocks 140a, 140b, 140c, and 140d. FIG. 8a shows data from sub-instruments 30a and 30b, where the data is not in phase. NDT-instrument supervisor 10 assumes that sub-instrument 30a is in the true time, although sub-instrument 30b, 30c, or 30d can also be used for the true time. The indication from sub-instrument 30b occurs later in time compared to sub-instrument 30a. NDT-instrument supervisor 10 then applies a cross-correlation function to the data from the two sub-instruments.

To correctly perform the cross-correlation, NDT-instrument supervisor 10 takes sample points before and after the indication for both sub-instrument 30a and sub-instrument 30b, and then performs the cross-correlation between the data from the sub-instruments. Assuming that N sample points are taken from each of sub-instruments 30a and 30b, then the length of the cross-correlation result is 2*N-1, which is depicted in FIG. 8a in the bottom right corner. If the data were in phase, the maximum of the cross-correlation would be attained at the sample "N", exactly the central sample of the Phase Detection Algorithm block of 2*N-1.

However, if the data from sub-instrument 30a and sub-instrument 30b are not in phase, the maximum is attained either before the sample N, or after the sample N. Therefore the position that is the maximum value needs to be determined. Simply taking the maximum value would yield a delay that is an integer multiple of the sampling period. However, instead of simply taking the maximum value of the cross-correlation output, a parabolic interpolation can be applied around the maximum sample in order to determine with better precision the actual delay between the 2 sub-instruments. The phase of the 2 sub-instruments can therefore be matched with precision in the nanosecond range.

FIG. 8b shows the result after application of the cross-correlation function to data from sub-instruments 30a and 30b, and correction of the phase difference. Referring to FIG. 8b, once the phase difference between sub-instrument 30a and sub-instrument 30b has been determined, it is easy to adjust the data between the 2 sub-instruments so that they are in phase. Delays that are greater than a sampling period are compensated by shifting the data from the sub-instrument that generates the "early" data.

Delays that are smaller than a sampling period can be compensated by using an all-pass delay filter, though other techniques exist. Such filters can be implemented in various ways, either in Infinite Impulse Response (IIR) topology or Fixed Impulse Response (FIR) topology. For example, if the indication is seen 25 nanoseconds earlier by sub-instrument 30a than sub-instrument 30b, and the sampling period of the instrument is 10 nanoseconds, a delay of 2 samples is applied on the data from sub-instrument 30a, and then a delay filter of 5 nanoseconds is applied. The total is a delay of 25 nanoseconds, making the data from sub-instrument 30a and sub-instrument 30b synchronous in phase. The process can be easily extended to 4 sub-instruments and more.

Returning to FIG. 7, the data in this design from sub-instruments 30a, 30b, 30c, and 30d is synchronized both in frequency and in phase. NDT-instrument supervisor 10 then time shifts the data from the data acquisition modules of the sub-instruments to make the data from Phase Detection Algorithm blocks 140a, 140b, 140c, and 140d start at the same time. Once this is done for the current data acquisition, remote instruments configurator 103 synchronizes the configuration modules of the sub-instruments to one another by data combiner 110, thereby creating a greater aperture from the sub-instruments for scan display module 120.

What is claimed is:

1. A non-destructive testing and inspection (NDT/NDI) system operable to conduct an NDT/NDI test operation on a test object with N number of testing areas, including areas 1, 2, . . . N, the inspection system comprising,
   a plurality of NDT/NDI instruments of the same type, including instruments 1, 2, . . . N, each coupled with a corresponding probe 1, 2, . . . N, which is further coupled with and receiving response signals from the corresponding testing area 1, 2, . . . , N, respectively, wherein each of the instruments has a corresponding operating clock 1, 2, . . . , N and a corresponding data acquisition unit 1, 2, . . . , N;
   a plurality of M clock managing units, wherein M is less than or equal to N, including clock managing units 1, 2, . . . , M, and,
   at least one supervising unit coupled with each of the instruments, and each supervising unit further comprising a data processing unit;
   wherein the clock managing units are configured to produce at least one predetermined clock and phase command managing at least one corresponding operating clock, and each clock managing unit is coupled to at least one corresponding instrument to operate the instrument with the predetermined clock and phase command, and the data processing unit is operable to compose an inspection result merging the response signals from at least some of the probes.

2. The inspection system of claim 1 wherein the clock managing units each further comprise a corresponding clock generation module, namely clock generation modules 1, 2, . . . , M and trigger generation modules, namely, trigger generation modules 1, 2, . . . M.

3. The inspection system of claim 2, wherein the clock generation modules are configured to each have a synchronization clock, according to which the corresponding operating clock of the at least one correspondingly coupled instrument is operated.

4. The inspection system of claim 2, wherein the clock generation module uses its own predetermined clock as the operating clock.

5. The inspection system of claim 3, wherein the predetermined clock and phase command is to have all the operating clocks to be at the same rate as the synchronization clock and to be in phase with each other.

6. The inspection system of claim 3 wherein each trigger generation module is configured to control each corresponding data acquisition unit of the correspondingly coupled instrument so that the triggering of all data acquisition units is within a time threshold.

7. The inspection system of claim 3, wherein the clock generation module (i) is coupled with clock generation module (i-1) and clock generation module (i+1) in daisy-chain fashion.

8. The inspection system of claim 7, wherein the clock generation module (i) has a phase lag behind the immediately connected clock generation module (i-1), and the clock generation module (i) is configured to compensate the phase lag and to instruct the operating clock (i) to be operated at the same phase as operating clock (i-1).

9. The inspection system of claim 7, wherein the clock generation module (i-1) sends the synchronization clock to its immediately connected clock generation module (i).

10. The inspection system of claim 7, wherein the phase lag is determined prior to the test operation and is substantially determined by the data transmission means and time delay between instruments (i-1) and (i).

11. The inspection system of claim 10, wherein the clock managing units are connected to each other via electronic cables for which the lag is substantially related to the lengths of the corresponding cable.

12. The inspection system of claim 10, wherein the clock managing units are connected to each other via wireless connections with the assistance of the Global Positioning System (GPS) and the associated phase lag between the clock managing units can be compensated after the acquisition is performed.

13. The inspection system of claim 3, wherein the clock generation module (i) has a phase lag behind the immediately connected clock generation module (i−1), and the phase lag is stored in a phase delay adjustment module in the at least one supervising unit so that the supervising unit is operable to compensate the phase lag when composing the inspection result.

14. The inspection system of claim 1 further comprising at least one local oscillator providing an internal clock for each corresponding clock generation module.

15. The inspection system of claim 14, wherein the clock managing unit adjusts the corresponding internal clock of the corresponding sub-instrument according to the predetermined clock and phase command.

16. The inspection system of claim 1, wherein the clock managing units are circuits external to the correspondingly coupled instruments.

17. The inspection system of claim 1, wherein the clock managing units are an integral part of the corresponding coupled instruments and are within the same enclosures of the correspondingly coupled instruments.

18. The inspection system of claim 1, wherein the clock managing units utilize phase-locked loop logical circuits (PLLs).

19. The inspection system of claim 1, wherein the at least one supervising unit is a supervising instrument of the same type as the plurality of NDT/NDI instruments.

20. The inspection system of claim 1, wherein each of the at least one supervising unit is part of one of the NDT/NDI instruments.

21. The inspection system of claim 1, wherein the at least one supervising unit and the NDT/NDI instruments are configured so that the supervising unit is operable to configure the instruments according to one or more of the following: the types of the instruments, the type of material of the test objects, the geometric characteristics of the test objects and the relative placement of the sub-instruments.

22. The inspection system of claim 1 wherein the inspection system is an ultrasonic inspection system and each of the instruments is an ultrasonic inspection instrument, and each of the probes is an ultrasonic probe.

23. The inspection system of claim 22, wherein the ultrasonic inspection system is a phased-array ultrasonic inspection system and each of the instruments is a phased-array ultrasonic inspection instrument, an d each of the probes is a phased-array ultrasonic probe.

24. The inspection system of claim 23, wherein the at least one supervising unit of each of the probes is configured to have apertures of ultrasonic probe elements and the system is configured to use one or more apertures of the probe to inspect the corresponding testing area.

* * * * *